United States Patent
Puder et al.

(10) Patent No.: US 9,109,005 B2
(45) Date of Patent: Aug. 18, 2015

(54) METHOD FOR MANUFACTURING OF CICLESONIDE

(71) Applicants: Carsten Puder, Ingelheim am Rhein (DE); Joern Merten, Heidesheim (DE); Heinz-Peter Schmitt, Ingelheim am Rhein (DE); Markus Thumerer, Mainz (DE); Bjoern Weyell, Aspisheim (DE)

(72) Inventors: Carsten Puder, Ingelheim am Rhein (DE); Joern Merten, Heidesheim (DE); Heinz-Peter Schmitt, Ingelheim am Rhein (DE); Markus Thumerer, Mainz (DE); Bjoern Weyell, Aspisheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 108 days.

(21) Appl. No.: 13/767,902

(22) Filed: Feb. 15, 2013

(65) Prior Publication Data

US 2013/0225804 A1    Aug. 29, 2013

(30) Foreign Application Priority Data

Feb. 23, 2012   (EP) .................................... 12156672

(51) Int. Cl.
*C07J 71/00* (2006.01)
(52) U.S. Cl.
CPC .................................. *C07J 71/0031* (2013.01)
(58) Field of Classification Search
CPC .................................................. C07D 71/0031
USPC ....................................... 540/63, 68
See application file for complete search history.

(56) References Cited

U.S. PATENT DOCUMENTS

| 3,718,673 A | 2/1973 | Ripka |
| 5,733,901 A | 3/1998 | Gutterer |
| 2013/0225804 A1 | 8/2013 | Puder et al. |

FOREIGN PATENT DOCUMENTS

| CN | 102477064 A | 5/2012 |
| WO | 9422899 A1 | 10/1994 |
| WO | 2008035066 A2 | 3/2008 |
| WO | 2009112557 A2 | 9/2009 |

OTHER PUBLICATIONS

Chemical Abstracts Services, Database Accession No. 2012:782620, 2010, 3 pages.
International Search Report and Written Opinion for PCT/EP2013/053516 mailed Apr. 10, 2013.
Abstract in English for CN102477064, 2012.

*Primary Examiner* — Brenda Coleman
(74) *Attorney, Agent, or Firm* — Michael P. Morris; Mary-Ellen M. Devlin

(57) ABSTRACT

The invention relates to a process for preparing the corticosteroid ciclesonide, used for the treatment of respiratory complaints, in epimerically pure form of formula 1:

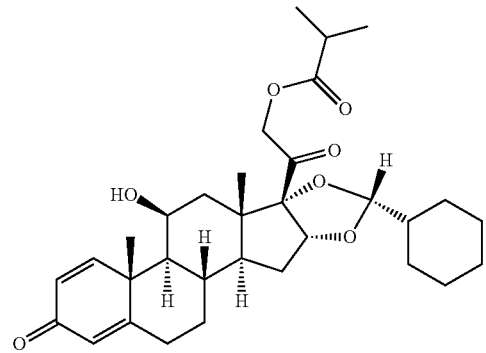

8 Claims, No Drawings

METHOD FOR MANUFACTURING OF CICLESONIDE

The invention relates to a process for preparing ciclesonide 1 (16α,17-[(R)-cyclohexylmethylenedioxy]-11β-hydroxy-21-(2-methyl-1-oxopropoxy)-pregna-1,4-dien-3,20-one) in epimerically pure form. This compound is a corticosteroid which has the following structure:

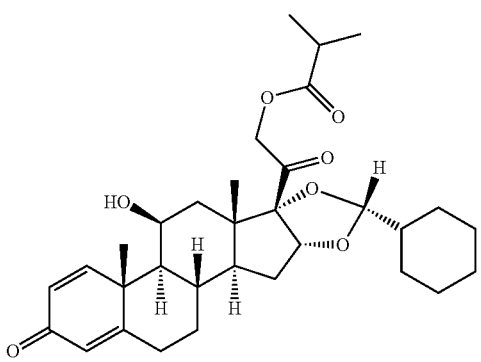

1

Ciclesonide is used for the treatment of respiratory complaints.

PRIOR ART

The synthesis and purification of the active substance and particular aspects of the synthesis have already been described in different studies:

DE 4129535 discloses the reaction of 11β,16α,17,21-tetrahydroxypregna-1,4-dien-3,20-one with isobutyric anhydride in pyridine to form the 16,17,21-triester and the subsequent reaction thereof with cyclohexane aldehyde in dioxane in the presence of hydrogen chloride and perchloric acid to obtain R,S-ciclesonide with R/S approx. 1:1. The reaction time for the second step is very long, at approx. 200 h.

WO 94/22899 discloses the synthesis of the intermediate 16α,17-[(R,S)-cyclohexylmethylenedioxy]-11β,21-dihydroxy-pregna-1,4-dien-3,20-one by acid-catalysed reaction of 11β,16α,17,21-tetrahydroxypregna-1,4-dien-3,20-one with cyclohexane aldehyde. Depending on the reaction conditions the epimer ratio of R/S in the crude product varies between 95:5-25:75. In the majority of the Examples listed the potentially explosive 70% perchloric acid is used as catalyst and in one Example it is even used as solvent. The handling of concentrated perchloric acid has resulted in the past in numerous accidents with fatal consequences (cf. e.g. L. Roth, U. Weller-Schäferbarthold, Gefährliche Chemische Reaktionen CD-ROM, August 2011 edition, ecomed Sicherheit), i.e. the occupational handling of this substance requires particularly stringent safety precautions and is therefore costly. In some Examples, nitromethane is used as solvent, which is another explosive substance.

WO 95/24416 discloses a process for concentrating the R epimer from 16α,17-[(R,S)-cyclohexylmethylenedioxy]-11β,21-dihydroxy-pregna-1,4-dien-3,20-one. Silylation in position 21, at least one fractional crystallisation and acid hydrolysis are necessary here in order to achieve a concentration of the R epimer to ≥97%.

WO 98/09982 discloses the fractional crystallisation of R,S-ciclesonide from mixtures of water-miscible solvents and water. Four successive crystallisations from ethanol/water are needed in order to achieve a total yield for the epimer purification of approx. 50%—starting from an epimer ratio of R/S of approx. 90:10—to a proportion of R>99.5%.

WO 02/38584 discloses the synthesis of 16α,17-[(R,S)-cyclohexylmethylenedioxy]-11β,21-dihydroxy-pregna-1,4-dien-3,20-one and R,S-ciclesonide with R/S>90:10 by reacting the corresponding 16,17-ketals with cyclohexane aldehyde in the presence of 70% perchloric acid. 1-Nitropropane is used as solvent. As already mentioned above, the use of concentrated perchloric acid has in the past resulted in a number of accidents with fatal consequences.

WO 2004/085460 centres on the preparation of fine crystalline material by the addition of a solution of R,S-ciclesonide in a water-miscible solvent to water. No concentration of the R epimer is observed during this process.

WO 2005/044759 relates to the synthesis of 16,17-acetals or 16,17-ketals of various pregnane derivatives by reacting the corresponding 16,17-dihydroxy compounds with aldehydes, acetals, ketones or ketals in 85% phosphoric acid. The reaction of 11β,16α,17,21-tetrahydroxypregna-1,4-dien-3,20-one with 2.5 equivalents of cyclohexane aldehyde in 4 parts of 85% phosphoric acid at 0-5° C., which is not described experimentally in WO 2005/044759, leads to a very unfavourable epimer ratio, as our own investigations have shown. After 5 h reaction and subsequent precipitation of the product by the addition of methanol and water, 16α,17-[(R,S)-cyclohexylmethylenedioxy]-11β,21-dihydroxy-pregna-1,4-dien-3,20-one is obtained with an R/S ratio of approx. 48:52.

WO 2007/054974 discloses the synthesis of 16α,17-[(R,S)-cyclohexylmethylenedioxy]-11β,21-dihydroxy-pregna-1,4-dien-3,20-one and similar compounds by acid-catalysed reaction of the corresponding 16,17-ketals with cyclohexane aldehyde in mixtures of ionic liquids with acetonitrile or dichloromethane. Depending on the reaction conditions the R/S epimer ratio in the isolated product varies between 92:8-78:22. In all the Examples provided the potentially explosive 70% perchloric acid is used as catalyst. The yields are between 137-213%, i.e. the purity of the isolated crude products is rather low.

WO 2007/056181 relates to the concentration of the R-epimer by crystallisation of R,S-ciclesonide from a solution containing at least one solvent that is water-immiscible. Four successive crystallisations from acetone/isooctane are needed in order to improve the R/S epimer ratio from approx. 90:10 to 99.75:0.25. Based on 45.9 g of product, more than 6137 g of acetone/isooctane are needed for the concentration process. When using dichloromethane/isooctane four crystallisations are needed to arrive at an R/S epimer ratio of 99.5:0.5, starting from an R/S epimer ratio of 90:10. Here again, a relatively large amount of solvent is used for the purification, namely more than 6000 g of dichloromethane/isooctane in relation to 37 g of product.

US 2007/0117974 centres on the acid-catalysed reaction of 11β,16α,17,21-tetrahydroxypregna-1,4-dien-3,20-one with carboxylic acid anhydrides and aldehydes to obtain 16,17-acetals acylated in position 21 in the form of a one-pot reaction. In all the examples provided 70% perchloric acid is used as the acid component. The required excess of anhydride (6 equivalents) and aldehyde (4 equivalents) is comparatively high.

WO 2008/015696 describes the chromatographic separation of R,S-ciclesonide into the two epimers using a chiral stationary phase. In all the examples a highly dilute solution is applied to the stationary phase (500 ppm, i.e. 1 g of epimer mixture dissolved in 2000 g solvent).

WO 2008/035066 relates to the acid-catalysed reaction of 11β,16α,17,21-tetrahydroxypregna-1,4-dien-3,20-one and derivatives of 11β,16α,17,21-tetrahydroxypregna-1,4-dien-3,20-one acylated in position 21 with the bisulphite adduct of cyclohexane aldehyde to form the corresponding 16,17-acetals. A disadvantage of this process is that the bisulphite adduct has to be prepared from cyclohexane aldehyde and sodium disulphite in a separate reaction step. This includes the isolation and drying of the bisulphite adduct. The reaction of acetalisation is carried out in the examples described using large amounts of 70% perchloric acid, which requires a great many safety precautions. Moreover, WO 2008/035066 describes a crystalline methanol solvate of ciclesonide, which is obtained by crystallisation of the active substance from methanol.

WO 2009/112557 describes the reaction of 11β,16α,17,21-tetrahydroxypregna-1,4-dien-3,20-one, 21-acetoxy-11β,16α,17-trihydroxy-pregna-1,4-dien-3,20-one or 11β,16α,17-trihydroxy-21-(2-methyl-1-oxopropoxy)-pregna-1,4-dien-3,20-one with cyclohexane aldehyde in the presence of bromine or hydriodic acid to form the corresponding 16,17-acetals. In the synthesis of 16α,17-[(R,S)-cyclohexylmethylenedioxy]-11β,21-dihydroxy-pregna-1,4-dien-3,20-one, in the first processing step the reaction mixture based on 1 g of 11β,16α,17,21-tetrahydroxypregna-1,4-dien-3,20-one used is added to 50 g of ice water, i.e. it is highly diluted.

A disadvantage of the methods of synthesis known in the art is that they are either only partly or not at all designed for large-scale industrial production and the special requirements in terms of the production of ciclesonide on a large scale have not been sufficiently taken into account. Looking at the aspects of safety at work, scale-up capability and use of resources (in terms of raw materials) it becomes clear that the prior art has not hitherto described any process that addresses these points adequately.

The present invention is thus based on providing an improved method of synthesis, particularly for use on an industrial scale, which enables pure ciclesonide to be produced safely and efficiently. The advantages of the present process are:

- use of a stable salt of isobutyric acid instead of hydrolysis-prone isobutyric acid derivatives such as e.g. isobutyric anhydride or isobutyric acid chloride.
- depletion of the 22S-epimer is possible at the 21-bromo-16α,17-cyclohexylmethylenedioxy-11β-hydroxypregna-1,4-dien-3,20-one stage.
- no perchloric acid and nitroalkanes are used in the preparation of ciclesonide.
- high total yield: by way of example mention may be made here of the total yield obtained with mixture A in Examples 1-6 (cf. the Experimental Section), which is approx. 38% starting from 11β,16α,17,21-tetrahydroxypregna-1,4-dien-3,20-one.

DETAILED DESCRIPTION OF THE INVENTION

The present invention relates to a process for preparing ciclesonide of formula 1,

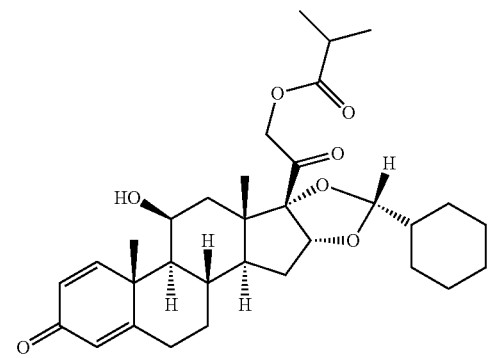

characterised in that a compound of formula 2

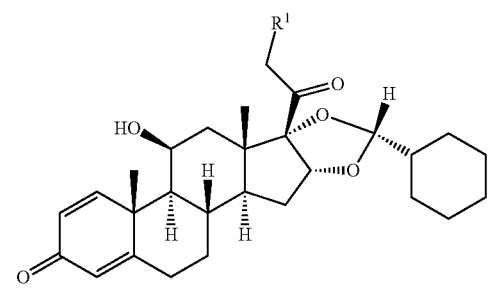

wherein $R^1$ may denote Br, I or Cl, is reacted with a salt of formula

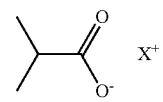

wherein $X^+$ denotes alkali metal ions, preferably selected from among $Li^+$, $Na^+$, $K^+$ and $Cs^+$, preferably $Na^+$; or $N(R^2)_4^+$, wherein $R^2$ denotes $C_{1-6}$-alkyl, preferably selected independently of one another from among methyl, ethyl, n-propyl, n-butyl and tert-butyl, preferably methyl and n-butyl.

Preferably, in the above process, $R^1$ in the compound of formula 2 denotes Br.

Preferably, in the above process, $X^+$ denotes $Li^+$, $Na^+$, $K^+$ or Cs+, preferably $Na^+$.

Preferably in the above process, $X^+$ denotes $N(R^2)_4$ and $R^2$ may be selected independently of one another from among methyl, ethyl, n-propyl, n-butyl and tert-butyl, preferably methyl and n-butyl.

Solvents that may be used for the above-mentioned reaction step include polar aprotic solvents [e.g. dimethylsulphoxide (DMSO), N-methyl-2-pyrrolidone (NMP), N-ethyl-2-pyrrolidone (NEP), dimethylformamide (DMF) and dimethylacetamide (DMAC)], polar ethers [e.g. tetrahydrofuran (THF), dioxane], polar nitriles (e.g. acetonitrile) and polar ketones (e.g. acetone). Preferred solvents for the reaction are dimethylsulphoxide, N-methyl-2-pyrrolidone, dimethylfomamide or mixtures thereof.

In one embodiment of the invention the above-mentioned reaction of compound 2 to obtain compound 1 is carried out at a reaction temperature of 20-70° C., preferably 35-55° C.

Preferably, in the above process, after the reaction has taken place the compound of formula 1 is purified by one or more, preferably one, two or three crystallisations from an alcoholic solvent, preferably ethanol or methanol/ethanol mixtures.

A preferred variant of the purification is a single or repeated crystallisation from a methanol/ethanol mixture with the preferred ratio between 2:1 and 1:2, preferably about 1:1, followed by crystallisation from ethanol.

Preferably, in the above process, the compound of formula 2,

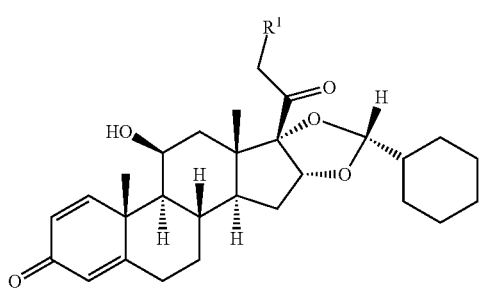

wherein $R^1$ denotes Br, is prepared by regioselective bromination of the compound of formula 3,

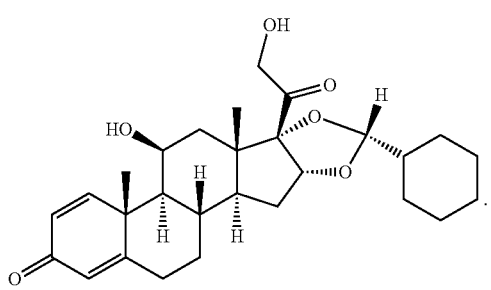

Preferably in the above process the regioselective bromination of the compound of formula 3 is carried out with a catalytic variant of the Appel reaction (cf. J. Org. Chem. 2011, 76, 6749-6767 and Chem. Eur. J. 2011, 17, 11290-11295); with phosphorus tribromide ($PBr_3$), with bromotriphenylphosphonium bromide ($BrPPh_3Br$) or with mixtures of organic triphenylphosphines, preferably $PPh_3$, and an agent selected from among N-bromosuccinimide (NBS), tetrabromomethane ($CBr_4$), hexabromoacetone ($CBr_3COCBr_3$), dibromo-Meldrum's acid (5,5-dibromo-2,2-dimethyl-4,6-dioxo-1,3-dioxane) and bromine ($Br_2$), preferably with $BrPPh_3Br$ or with mixtures of triphenylphosphine and a brominating agent selected from among N-bromosuccinimide, tetrabromomethane, hexabromoacetone and $Br_2$, particularly N-bromosuccinimide.

Preferably in the above process the regioselective bromination of the compound of formula 3 is carried out in a solvent selected from among halohydrocarbons, nitriles and mixtures of halohydrocarbons and nitriles. Examples of nitriles might be: acetonitrile and propionitrile. Examples of halohydrocarbons might be: dichloromethane, 1,2-dichloroethane and chloroform.

Preferably in the above process the regioselective bromination of the compound of formula 3 is carried out in a solvent selected from among dichloromethane, acetonitrile and dichloromethane/acetonitrile mixtures.

In the bromination with N-bromosuccinimide (NBS)/ triphenylphosphine ($PPh_3$) the use of 1 to 2 equivalents of the $NBS/PPh_3$ mixture in relation to the educt is preferred. It is particularly preferable to use 1.2 to 1.5 equivalents of the $NBS/PPh_3$ mixture.

It has been found that for the $NBS/PPh_3$ mixture a ratio of 1:1 or a small excess of NBS over $PPh_3$ is advantageous. The excesses of NBS and $PPh_3$ may, however, also be of different sizes according to the invention (e.g. 1.25 eq. NBS:1.25 eq. $PPh_3$; 1.35 eq. NBS:1.35 eq. $PPh_3$; 1.45 eq. NBS:1.45 eq. $PPh_3$; 1.50 eq. NBS:1.50 eq. $PPh_3$; 1.35 eq. NBS:1.20 eq. $PPh_3$; 1.35 eq. NBS:1.25 eq. $PPh_3$; 1.45 eq. NBS:1.25 eq. $PPh_3$; 1.50 eq. NBS:1.30 eq. $PPh_3$; 1.50 eq. NBS:1.35 eq. $PPh_3$).

Preferably, the above process is characterised in that the compound of formula 2, wherein $R^1$ denotes Br, is purified after the reaction by one or more, preferably one or two, crystallisations from a polar, water-miscible, organic solvent or mixtures thereof, with or without the addition of water; preferred are mixtures of solvents selected independently of one another from among methanol, ethanol, isopropanol, acetonitrile, N-methyl-2-pyrrolidone (NMP), N-ethyl-2-pyrrolidone (NEP), dimethylformamide (DMF), dimethylacetamide (DMAC), dimethylsulphoxide (DMSO), acetone, methylethylketone (MEK), tetrahydrofuran (THF), dioxane, or other water-miscible ethers and water; preferred are mixtures of solvents selected independently of one another from among methanol, acetonitrile, NMP, NEP, DMSO, acetone, THF, MEK and water; preferred are mixtures of solvents selected independently of one another from among methanol, acetonitrile, NMP, DMSO, acetone and water.

In one embodiment according to the invention the mixtures of solvents consist of two or three, preferably two solvents of the examples mentioned above.

In one embodiment according to the invention of the above process for preparing the compound of formula 2 wherein $R^1$ denotes Br, after the reaction, for purification there is
  a) a first crystallisation from a polar, water-miscible organic solvent or mixtures thereof, with or without the addition of water; preferably mixtures of solvents are used selected independently of one another from among methanol, acetonitrile and water;
followed by
  b) at least one purification by suspension in a polar, water-miscible organic solvent or mixtures thereof, with or without the addition of water; preferably mixtures of solvents are used selected independently of one another from among acetonitrile, NMP, NEP, DMF, DMAC, DMSO, acetone, MEK, THF, dioxane or other water-miscible ethers and water, preferably acetonitrile, NMP, NEP, DMF, DMAC, DMSO, acetone, MEK, THF and water, preferably acetonitrile, NMP, DMSO, acetone and water.

If necessary, step b) may be repeated until the R epimer has been suitably concentrated. Preferably, there is a proportion of more than 95%, preferably 96%, preferably 97% of the R epimer in the product mixture of the compound of formula 2, wherein $R^1$ denotes Br.

Step b) may be carried out selectively at low temperatures (e.g. ambient temperature) or high temperatures (boiling point). Preferably, the temperature is between 40° C. and boiling point, preferably between 45 and 80° C., depending on the boiling point of the solvent or mixture of solvents used.

In one embodiment according to the invention the mixtures of solvents in steps a) and b) consist of two or three, preferably two solvents of the examples mentioned therein.

Preferably in the above process the compound of formula 3 is obtained by a reaction of the compound of formula 4

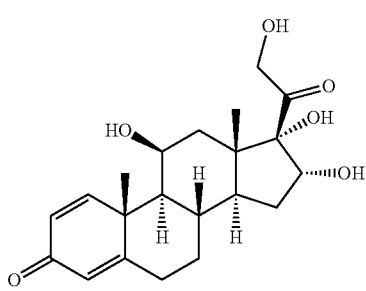

4 with cyclohexane aldehyde in the presence of an acid, preferably methanesulphonic acid. The use of acids as catalyst and suitable solvents in the reaction of a compound of formula 4 with cyclohexane aldehyde has already been described in WO 94/22899, to which reference is hereby made in its entirety.

Preferably in the above process the product of formula 3 is not isolated but reacted further directly to form a compound of formula 2.

TERMS AND DEFINITIONS USED

Compound 1 within the scope of the invention denotes ciclesonide or 16α,17-[(R)-cyclohexylmethylenedioxy]-11β-hydroxy-21-(2-methyl-1-oxopropoxy)-pregna-1,4-dien-3,20-one:

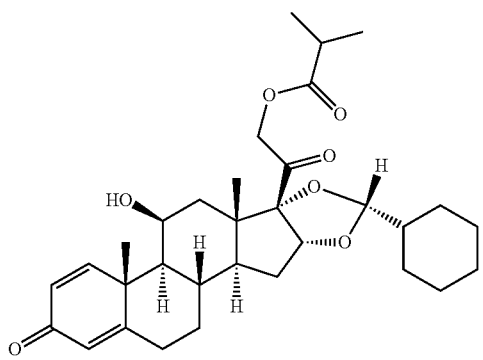

1

The term R,S-ciclesonide within the scope of the invention denotes 16α,17-[(R,S)-cyclohexylmethylenedioxy]-11β-hydroxy-21-(2-methyl-1-oxopropoxy)-pregna-1,4-dien-3,20-one:

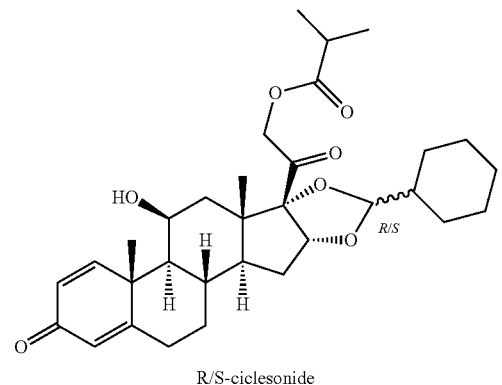

R/S-ciclesonide

The partial term "R,S" in the name of R,S-ciclesonide and 16α,17-[(R,S)-cyclohexylmethylenedioxy]-11β-hydroxy-21-(2-methyl-1-oxopropoxy)-pregna-1,4-dien-3,20-one denotes that it is an epimer mixture (mixture of diastereomers), but the ratio of epimers cannot be inferred from this, i.e. "R,S" does not mean that there has to be an epimer ratio of R/S 1:1.

Compound 2 within the scope of the invention denotes 21-bromo-16α,17-[(R)-cyclohexylmethylenedioxy]-11β-hydroxypregna-1,4-dien-3,20-dione.

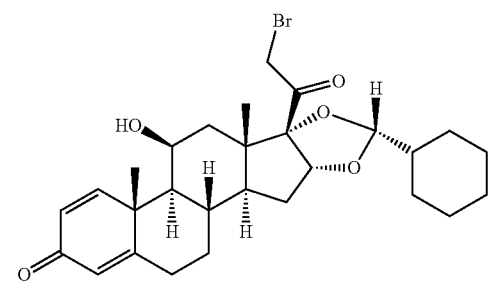

2

Compound 3 within the scope of the invention denotes 16α,17-[(R)-cyclohexylmethylenedioxy]-11β,21-dihydroxy-pregna-1,4-dien-3,20-one.

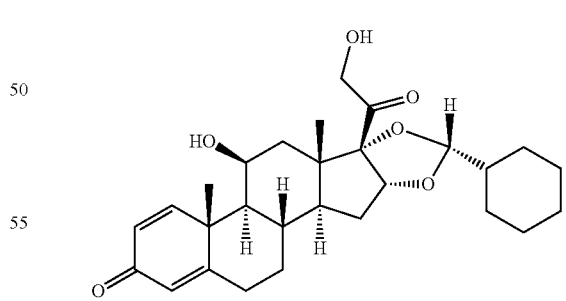

3

Unless otherwise stated, all the substituents are independent of one another. If for example a plurality of $C_{1-6}$-alkyl groups were to be present as substituents on one group, then, in the case of three $C_{1-6}$-alkyl substituents, they could independently of one another represent one methyl, one n-propyl and one tert-butyl.

Unless stated otherwise, in organic compounds the groups R″, wherein n is a placeholder for a means for distinguishing different groups R, replace the hydrogen atoms that are not usually shown. If a group R″ in a formula is given as a substituent of a carbon atom, this group R″ may replace one or more hydrogen atoms, depending on the definition. Thus, for example, in the following formula by way of example

the group R″ may denote OH and hence the formula itself may denote 2-propanol. However, if the group R″ denotes O or, written another way, =O, two hydrogen atoms are replaced and the formula itself denotes acetone in this example.

Also included in the subject-matter of this invention are the compounds according to the invention, including the salts thereof, wherein one or more hydrogen atoms, for example one, two, three, four or five hydrogen atoms, are replaced by deuterium.

By an "organic solvent" is meant within the scope of the invention an organic, low-molecular substance which may dissolve other organic substances by a physical method. A prerequisite for suitability as a solvent is that during the dissolving process neither the dissolving substance nor the dissolved substance may change chemically, i.e. the components of the solution may be recovered in their original form by physical methods of separation such as distillation, crystallisation, sublimation, vaporisation or adsorption. For various reasons not only the pure solvents but also mixtures that combine the dissolving properties may be used. Examples include:

- alcohols (alcoholic solvents), preferably methanol, ethanol, propanol, butanol, octanol, cyclohexanol;
- glycols, preferably ethyleneglycol, diethyleneglycol;
- ethers/glycolethers, preferably diethyl ether, methyl-tert-butylether, dibutylether, anisol, dioxane, tetrahydrofuran, mono-, di-, tri-, polyethyleneglycolether;
- ketones, preferably acetone, butanone, cyclohexanone;
- esters, preferably acetic acid esters, glycolesters;
- amides, including nitrogen compounds, preferably dimethylformamide, pyridine, N-methyl-2-pyrrolidone, acetonitrile;
- nitro compounds, preferably nitrobenzene;
- halohydrocarbons, preferably dichloromethane, chloroform, tetrachloromethane, trichlorethene, tetrachlorethene, 1,2-dichloroethane, chlorofluorocarbons;
- aliphatic or alicyclic hydrocarbons;
- aromatic hydrocarbons, preferably benzene, toluene, o-xylene, m-xylene, p-xylene;

or corresponding mixtures thereof.

By the term "$C_{1-6}$-alkyl" (including those that are part of other groups) are meant branched and unbranched alkyl groups with 1 to 6 carbon atoms and by the term "$C_{1-4}$-alkyl" are meant branched and unbranched alkyl groups with 1 to 4 carbon atoms. Alkyl groups with 1 to 4 carbon atoms are preferred. Examples include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. may optionally also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

In purification by "suspension" a crude product obtained in solid form is stirred with a suitable solvent and washed out. The solvent is suitable, under the conditions selected, for dissolving impurities from the crude product, but dissolves the product itself only to a very minor extent or ideally not at all. However, should some of the product become dissolved, it can usually be recovered analogously to a purification by recrystallisation by cooling the solution. In principle, the same solvents may be used for the suspension as are used for purification by recrystallisation, but because of the small amounts used or the fact that the temperature is too low they are not capable of dissolving the product completely. After washing out, the suspension is filtered to recover the product.

EXPERIMENTAL SECTION

Example 1

Preparation of Compound 3 (Concentrate)

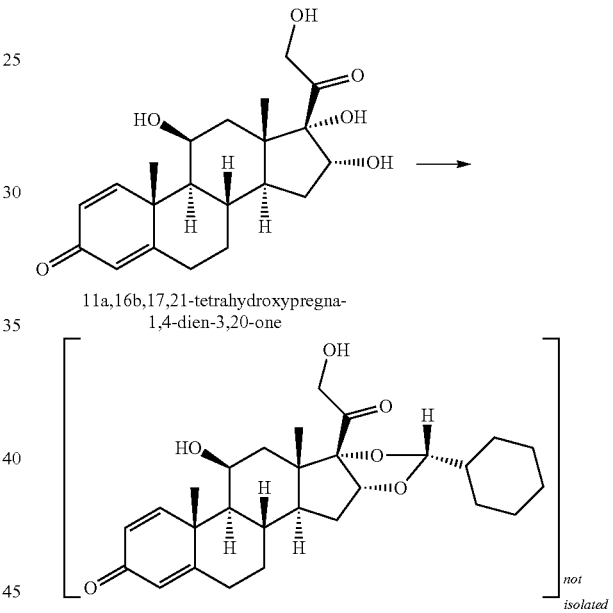

Mixture A: 100 g of 11β,16α,17,21-tetrahydroxypregna-1,4-dien-3,20-one are suspended in 2 l of dichloromethane, cooled to −20° C. and 37 g cyclohexane aldehyde are added with stirring. Then 255 g of methanesulphonic acid are added within 30 min at this temperature. The solution thus obtained is stirred for 3 h at −20° C. The reaction solution is combined with a mixture of 160 ml of 45% sodium hydroxide solution and 500 ml of water at max. 10° C. and then adjusted to a pH of 8.5 with 100 ml of 5% sodium hydrogen carbonate solution. The phases are separated from one another and the aqueous phase is extracted once with 500 ml dichloromethane. The combined organic phases are washed once with 500 ml of water and then concentrated down to a volume of 900 ml.

Mixture B: 255 g methanesulphonic acid are added to a mixture of 100 g of 11β,16α,17,21-tetrahydroxypregna-1,4-dien-3,20-one, 2 l of dichloromethane and 37 g of cyclohexane aldehyde at −10 to −15° C. within 30 min. The solution is stirred for 3 h at −15° C. and then adjusted to pH 8 with approx. 10% sodium hydroxide solution, the phases are separated from one another and the aqueous phase is extracted once with 500 ml of dichloromethane. The combined organic phases are washed once with 500 ml of water and then concentrated to a total volume of 900 ml.

Mixture C: 25 g of 11β,16α,17,21-tetrahydroxypregna-1,4-dien-3,20-one and 500 ml of dichloromethane are taken and first 9 g cyclohexane aldehyde are added quickly at −15° C. and then a total of 64 g methanesulphonic acid are added at −18 to −20° C. within 30 min, with stirring. After approx. 3 h at −20° C. the reaction solution is adjusted to a pH of 2.5 with a mixture of 40 ml of 45% sodium hydroxide solution and 125 ml of water and then to a pH of 8.5 with 25 ml of 5% sodium hydrogen carbonate solution. The phases are separated from one another and the aqueous phase is extracted once with 125 ml of dichloromethane. The combined organic phases are washed once with 125 ml of water and concentrated in vacuo to a volume of 225 ml.

Mixture D: 700 g of 11β,16α,17,21-tetrahydroxypregna-1,4-dien-3,20-one and 7 l of dichloromethane are placed in a 25 l reactor. The suspension is cooled to −15° C. with stirring and at this temperature 258 g cyclohexane aldehyde are metered in. Within 30 minutes 1790 g of methanesulphonic acid are added and the resulting solution is stirred for 160 min at −15° C. The reaction mixture is adjusted at max. 10° C. to a pH of 1.8 with a solution of 1.1 l of 45% sodium hydroxide solution and 5.8 l water and then adjusted to a pH of 8.0 with a 5% sodium hydrogen carbonate solution. The phases are separated from one another and the aqueous phase is extracted once with 3.7 l of dichloromethane. Then the combined organic phases are washed once with 3.5 l of water and the product solution is evaporated down to a volume of 5 l under a pressure of approx. 600 mbar and a jacket temperature of max. 50° C.

Mixture E: 700 g of 11β,16α,17,21-tetrahydroxypregna-1,4-dien-3,20-one and 7 l of dichloromethane are placed in a 25 l stirred apparatus. The contents of the apparatus are cooled to −15° C. with stirring and 258 g of cyclohexane aldehyde are added. Then within 30 minutes 1790 g methanesulphonic acid are metered in and the resulting solution is stirred for a further 210 min at −15° C. The reaction mixture is combined with a solution of 1.1 l of 45% sodium hydroxide solution and 5.8 l of water at max. 10° C. and then adjusted to a pH of 8.0 with 1.8 l of a 5% sodium hydrogen carbonate solution. The phases are separated and the aqueous phase is extracted once with 3.5 l dichloromethane. The combined organic phases are washed once with 3.5 l of water and some of the solvent is distilled off at a pressure of approx. 600 mbar and a jacket temperature of max. 50° C. 5 l of compound 3 concentrate are obtained.

Mixture F: 15 g cyclohexane aldehyde are added to a suspension of 40 g of 11β,16α,17,21-tetrahydroxypregna-1,4-dien-3,20-one in 400 ml dichloromethane and the mixture is cooled to −17° C. At this temperature 102 g methanesulphonic acid are metered in with stirring within 35 min. The resulting solution is stirred for a further 3 h, and at the end of the stirring time the temperature is 0° C. The reaction mixture is neutralised with a solution of 64 ml of 45% sodium hydroxide solution and 200 ml of water and then adjusted to a pH of 7.8 with approx. 5 ml of 5% sodium hydrogen carbonate solution. The phases are separated from one another, the aqueous phase is extracted once with 100 ml of dichloromethane and then the combined organic phases are washed once with 100 ml of water. The combined organic phases are worked up in mixture H of Example 2.

Example 2

Preparation of Compound 2 (Crude)

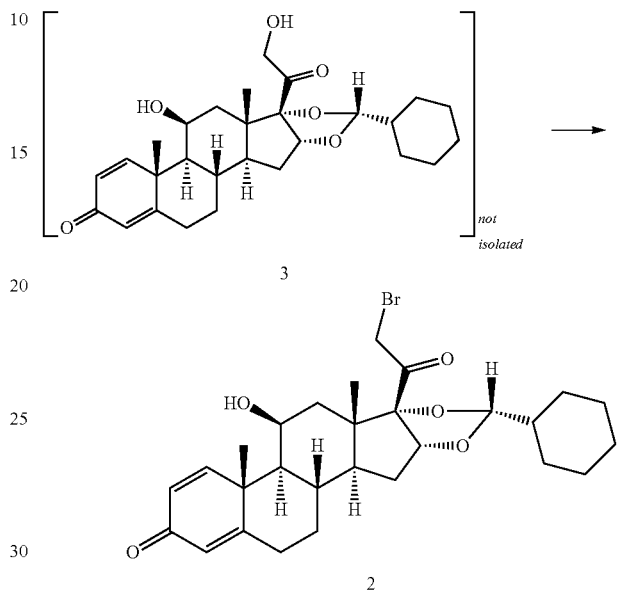

Mixture A: 300 ml of the concentrate of compound 3 (from Example 1, mixture A) are diluted with 480 ml of dichloromethane. 35 g of triphenylphosphine are added with stirring under an inert gas atmosphere and the solution is cooled to 10° C. In a temperature range from 10 to 16° C., 24 g of N-bromosuccinimide (NBS) are added batchwise within 1 h. After another hour the reaction mixture is evaporated to dryness, 50 ml of methanol are added and the mixture is evaporated to dryness again. Then the residue is taken up in 760 ml of methanol, 40 ml of water are added, the mixture is heated to 50° C. and stirred for 1 h. The resulting suspension is allowed to return slowly to ambient temperature. It is stirred for a further 16 h and the suspension is filtered through a suction filter. The solid separated off is washed twice with 25 ml of methanol/water 95:5 and twice with 25 ml of methanol and then dried at 60° C. in the vacuum dryer. 35 g compound 2 are obtained in crude form. Chromatographic purity (HPLC-UV): 93.5% fl. R epimer, 5.5% fl. S epimer.

Mixture B: 35 g of triphenylphosphine are added to 300 ml of the concentrate of compound 3 (from Example 1, mixture A) with stirring under an inert gas atmosphere, the mixture is cooled to 10° C. and then a solution of 24 g of N-bromosuccinimide in 480 ml acetonitrile is metered in at 10 to 16° C. within 1 h. After 1 h reaction time the reaction mixture is evaporated to dryness at 40° C. in vacuo, 50 ml of methanol are added and the mixture is evaporated to dryness once more. The remaining residue is taken up in 500 ml of methanol, combined with 26 ml of water and heated to 50° C. At this temperature it is stirred for 1 h, during which time the product begins to precipitate out. After cooling to ambient temperature the suspension is stirred for a further 16 h. The precipitate separated off by vacuum filtration is washed twice with 25 ml of methanol/water 95:5 and twice with 25 ml of methanol.

After drying at 60° C. in the vacuum dryer 36 g of the product is obtained. Chromatographic purity (HPLC-UV): 92.9% fl. R epimer, 5.6% fl. S epimer.

Mixture C: 450 ml of the concentrate of compound 3 (from Example 1, mixture B) and 52 g triphenylphosphine are taken at 15° C., a solution of 66 g tetrabromomethane in 660 ml dichloromethane is metered in within 90 min and the mixture is stirred for another 30 min at 15 to 20° C. The reaction mixture is evaporated to dryness in vacuo at 40° C., 50 ml of methanol are added and the solvent is distilled off once more. The residue is dissolved in 760 ml of methanol, combined with 40 ml of water and stirred for several hours at ambient temperature. The resulting suspension is cooled to 10° C. After 2 h at 10° C. the precipitated solid is separated off using a filtration device, washed with 100 ml of methanol and dried at 60° C. in the vacuum dryer. 50 g product are obtained. Chromatographic purity (HPLC-UV): 89.5% fl. R epimer, 7.9% fl. S epimer.

Mixture D: 450 ml of the concentrate of compound 3 (from Example 1, mixture B) are placed under an inert gas atmosphere and at 10° C. a suspension of 73 g bromotriphenylphosphonium bromide in 660 ml dichloromethane is added batchwise within 90 min. After the addition has ended the reaction mixture is stirred for another 30 min and then evaporated to dryness in vacuo. 50 ml of methanol are added to the residue and again the mixture is evaporated to dryness. The residue is taken up in a mixture of 760 ml of methanol and 40 ml of water, the resulting suspension is stirred first for several hours at ambient temperature, then cooled to 10° C. and stirred for another 2 h at 10° C. The precipitate separated off by suction filtering is washed with 100 ml of methanol and dried at 60° C. in the vacuum dryer. The yield is 45 g. Chromatographic purity (HPLC-UV): approx. 88.3% fl. R epimer, approx. 5.1% fl. S epimer.

Mixture E: the concentrate of compound 3 (225 ml) obtained from mixture C of Example 1 and 26 g triphenylphosphine are placed at 10° C. under an inert gas atmosphere and a solution of 18 g of N-bromosuccinimide in 480 ml dichloromethane is added with stirring at 10 to 16° C. within 1 h. After 1 hour's reaction the solvent is distilled off in vacuo at 40° C., the residue is combined with 50 ml of methanol and the solvent is distilled off again. The residue is taken up in 760 ml of methanol with gentle heating and combined with 40 ml of water. The resulting suspension is stirred for 1 h at 50° C. Then it is allowed to come up to ambient temperature and stirred for a further 16 h. The solid is separated off by vacuum filtration, washed twice with 25 ml of methanol/water 95:5 and twice with 25 ml of methanol and then dried at 60° C. in the vacuum dryer. 25 g product are obtained. Chromatographic purity (HPLC-UV): 93.8% fl. R epimer and 4.8% fl. S epimer.

Mixture F: 730 g of triphenylphosphine and 5 l of dichloromethane are added to the concentrate of compound 3 (5 l) obtained from mixture D of Example 1, with stirring, under an inert gas atmosphere, and the solution is cooled to 5° C. At 5 to 10° C., 496 g of N-bromosuccinimide are added in five batches within 1 h and stirred for a further 3 h. In the course of the second stirring period the reaction mixture is slowly heated from 10° C. to 20° C. and then the solvent is distilled off in vacuo at a jacket temperature of max. 50° C. The distillation residue is suspended in 1.4 l of methanol, the solvent is distilled off again in vacuo and then 10.5 l of methanol and 0.56 l of water are added. The resulting suspension is cooled from 40° C. to 20° C. within 2 h, stirred for a further 16 h at 20° C. and then added through a pressure filter. The filter cake obtained is washed with 0.70 l of methanol/water 95:5 and 0.70 l of methanol and then dried at 60° C. in vacuo. 660 g of compound 2 are obtained in crude form. Chromatographic purity (HPLC-UV): 91.9% fl. R epimer, 6.6% fl. S epimer; drying loss (80° C.): 0.3%.

Mixture G: the concentrate of compound 3 (5 l) obtained from mixture E of Example 1, 658 g of triphenylphosphine and 5 l of dichloromethane are placed in a 25 l reactor. The reactor contents are cooled to 5° C., 446 g of N-bromosuccinimide are added batchwise within 1 h at 5 to 10° C., the mixture is kept for 1 h at 10° C. and the reaction mixture is then allowed to come up to 20° C. within 3 h. The solvent is distilled off in vacuo at max. 50° C. jacket temperature, 1.4 l of methanol are added to the residue and it is distilled again. The residue remaining in the reactor is taken up in 10.5 l of methanol and 0.56 l of water and slowly cooled from 40° C. to 20° C. The resulting suspension is stirred for another 21 h at 20° C. and then the precipitate is isolated using a pressure filter. The precipitate is washed first with 0.70 l of methanol/water 95:5 and then with 0.70 l of methanol. After drying at 50° C. in vacuo, 740 g of the product is obtained. Chromatographic purity (HPLC-UV): 92.2% fl. R epimer, 6.5% fl. S epimer; drying loss (80° C.): 1.9%.

Mixture H: The combined organic phases from Mixture F of Example 1 are evaporated to dryness in vacuo, the non-volatile constituents are combined with 200 ml of acetonitrile and evaporated to dryness again at 40 to 50° C. The residue remaining is taken up in 500 ml acetonitrile and at 50° C., with stirring, 42 g triphenylphosphine and a further 250 ml acetonitrile are added under an inert gas atmosphere. The mixture is cooled to 2° C. and at this temperature 29 g of N-bromosuccinimide are added in 15 batches within 70 min. The mixture is stirred for another 3 h at 2 to 3° C. and allowed to come up to 12° C. within 90 min. The reaction mixture is evaporated down to a volume of approx. 260 ml and 13 ml of water are added at 45° C. After cooling to ambient temperature the resulting suspension is stirred for 16 h and then subjected to vacuum filtration. The isolated precipitate is washed twice with 50 ml acetonitrile and then dried at 60° C. in vacuo. 32 g of compound 2 are obtained in crude form. Chromatographic purity (HPLC-UV): 94.6% fl. R epimer, 4.2% fl. S epimer.

Example 3

Purification of Compound 2 (Crude) to Compound 2 (Industrial Grade)

Mixture A: 30 g of crude compound 2 (from Example 2, Mixture A) are suspended in a mixture of 588 ml of acetonitrile and 12 ml of N-methyl-2-pyrrolidone (NMP). The suspension is heated to 80° C. with stirring and kept for 1 h at this temperature. After slow cooling to 5° C. the mixture is kept for 16 h at this temperature and then added through a Büchner funnel. The precipitate separated off is washed with 50 ml of acetonitrile previously adjusted to a temperature of 5° C., and dried at 60° C. in vacuo. 23 g of industrial grade compound 2 are left. Chromatographic purity (HPLC-UV): 97.0% fl. R epimer, 2.7% fl. S epimer.

Mixture B: 250 g of crude compound 2 [chromatographic purity (HPLC-UV): approx. 91.9% fl. R epimer, approx. 5.8% fl. S epimer] are suspended in a mixture of 4.9 l of acetonitrile and 0.10 l of N-methyl-2-pyrrolidone, heated to 80° C. with stirring and kept for 1 h at this temperature. Then it is slowly cooled to 20° C. and the suspension is stirred for several hours at this temperature. It is then cooled to 5° C. and stirred for 1 h at this temperature. The solid is separated off through a suction filter, washed with 0.20 l of acetonitrile and dried for approx. 15 h in the vacuum dryer at 60° C. 195 g of product are obtained. Chromatographic purity (HPLC-UV): 95.8% fl. R epimer, 3.3% fl. S epimer.

Mixture C: 25 g of crude compound 2 [chromatographic purity (HPLC-UV): 89.6% fl. R epimer, 7.2% fl. S epimer] are combined with 500 ml of acetonitrile/dimethylsulphoxide 98:2 and stirred for 1 h at 80° C. The mixture is slowly cooled to 20° C. and then stirred for another 16 h at this temperature. The precipitate is filtered off through a Büchner funnel, washed with 25 ml of acetonitrile and dried for 20 h at 60° C. in vacuo. The yield is 20 g. Chromatographic purity (HPLC-UV): 95.2% fl. R epimer, 3.3% fl. S epimer.

Mixture D: a suspension of 212 g of crude compound 2 [chromatographic purity (HPLC-UV): approx. 92.2% fl. R epimer and approx. 4.7% fl. S epimer), 1000 ml of acetone and 50 ml of water is stirred for 2 h at 50° C. It is then allowed to come up to ambient temperature and stirred for several more hours at ambient temperature. The precipitate separated off is washed with 200 ml of acetone/water 90:10 and then dried for 20 h at 60° C. in the vacuum dryer. 163 g of product are obtained. Chromatographic purity (HPLC-UV): 97.4% fl. R epimer, 1.4% fl. S epimer.

Example 4

Preparation of Crude Ciclesonide

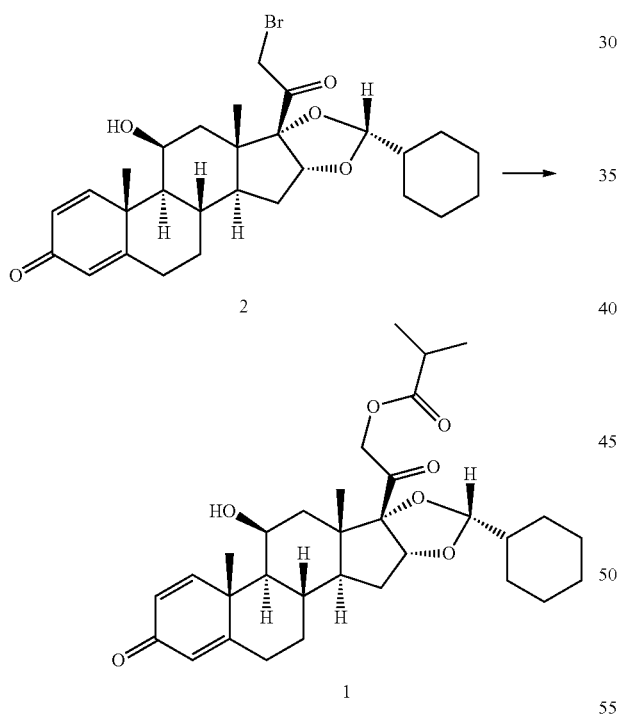

Mixture A: A mixture of 22 g of industrial-grade compound 2 (from Example 3, mixture A), 110 ml of DMSO and 6 g of sodium isobutoxide is heated to 40° C. with stirring. After 90 min the resulting reaction solution is allowed to cool to approx. 20° C. and 176 ml of methyl-tert-butylether (MtBE) and 110 ml of water are added. The mixture is stirred vigorously for 10 min, the organic and the aqueous phase are separated from one another and the aqueous phase is discarded. The organic phase is washed three times with 60 ml of water, evaporated to dryness in vacuo, 10 ml of ethanol are added and the mixture is again evaporated to dryness. Then the residue remaining is dissolved in 33 ml of ethanol at approx. 60° C., combined with 33 ml of methanol and slowly cooled to 0° C. The suspension is stirred for 3 h at 0° C. The precipitate is separated off by suction filtering, washed with 66 ml of cold methanol and dried at 70° C. in the vacuum dryer. 20 g of crude ciclesonide are obtained. Chromatographic purity (HPLC-UV): 98.8% fl. R epimer, 0.9% fl. S epimer.

Mixture B: 194 g of industrial-grade compound 2 (from Example 3, mixture B) are placed in 970 ml of dimethylsulphoxide (DMSO) at ambient temperature and 55 g of sodium isobutoxide are added with stirring. The reaction mixture is heated to 40° C., kept for 80 min at this temperature and then cooled to ambient temperature. After the addition of 1550 ml of methyl-tert-butylether and 970 ml of water the resulting 2-phase system is vigorously stirred for 10 min. After phase separation has been carried out the organic phase is washed three times with 530 ml of water and then the solvent is distilled off in vacuo. The residue remaining is taken up in 90 ml of ethanol and the solvent is distilled off again. The residue is dissolved at 60° C. in 290 ml of ethanol and combined with 290 ml of methanol. It is slowly allowed to return to ambient temperature and stirred for 15 h at this temperature. The suspension is cooled to 0° C. and kept for 2 h at this temperature. The solid is then separated off by vacuum filtration, washed with 580 ml of cold methanol and then suction filtered dry. 183 g of solid are obtained. Chromatographic purity (HPLC-UV): 98.5% fl. R epimer, 1.1% fl. S epimer; drying loss (70° C.): 2%.

Mixture C: 40 g of industrial-grade compound 2 [chromatographic purity (HPLC-UV): 93.4% fl. R epimer, 2.9% fl. S epimer] are dissolved in 220 ml of N-methyl-2-pyrrolidone and 11 g of sodium isobutoxide are added at ambient temperature. The reaction mixture is heated to 50° C., kept for 3 h at this temperature and then cooled to ambient temperature. 300 ml of methyl-tert-butylether and 200 ml of water are added and a high stirring speed is selected for 10 min. After separation of the two phases the aqueous phase is discarded. The organic phase is washed three times with 100 ml of water and evaporated to dryness in vacuo. The residue is taken up in 60 ml of ethanol in the warm, briefly distilled in vacuo, 60 ml of methanol are added and the mixture is left to cool slowly to ambient temperature. The resulting suspension is stirred for several hours at ambient temperature and then for 3 h at 0° C. The precipitate separated off by suction filtration is washed once with 30 ml and once with 50 ml of cold methanol and dried for 20 h at 60° C. in the vacuum dryer. 34 g of solid are obtained. Chromatographic purity (HPLC-UV): 97.7% fl. R epimer, 0.9% fl. S epimer.

Example 5

Purification of Ciclesonide (Crude) to Ciclesonide (Industrial Grade)

Mixture A: the crude ciclesonide (20 g) obtained from mixture A of Example 4 is dissolved in 33 ml of ethanol at 70° C. and combined with 33 ml of methanol with stirring. The solution is cooled to 2° C. within approx. 4 h and then left to stand for 16 h at 2° C. The product that crystallises out is separated off by suction filtering. The filter cake is washed twice with 20 ml of cold methanol and then dried for 20 h at 70° C. in vacuo. 18 g of industrial-grade ciclesonide are obtained. Chromatographic purity (HPLC-UV): 99.5% fl. R epimer, 0.4% fl. S epimer.

Mixture B: 181 g of crude ciclesonide (from Example 4, Mixture B) are suspended in 300 ml of ethanol at ambient temperature. During heating to 70° C. a solution is formed. 300 ml of methanol are added to this solution with stirring, it is cooled very slowly to 0° C. and the resulting crystal suspension is kept for 2 h at this temperature. The precipitate is separated off by suction filtering, the crystals are washed with 300 ml cold methanol and then suction filtered until thoroughly dry. 163 g of solid are obtained. Chromatographic purity (HPLC-UV): 99.4% fl. R epimer, 0.4% fl. S epimer; drying loss (70° C.): 2%.

Example 6

Purification of Ciclesonide (Industrial Grade) to Ciclesonide (Pure)

Mixture A: 170 mg of activated charcoal are added to a solution of 17 g of industrial-grade ciclesonide (from Example 5, Mixture A) which has been adjusted to a temperature of 70° C., in 24 ml of ethanol. A clear filtration is carried out and the filter residue is washed with 10 ml of ethanol. The combined filtrate is left to cool to 21° C. within 3 h. The resulting suspension is then cooled to 2° C. After 16 h at 2° C. the mixture is filtered and the precipitate is washed twice with 20 ml of cold ethanol. The isolated product is dried for 20 h at 60° C. in vacuo. The yield of pure ciclesonide is 14 g. Chromatographic purity (HPLC-UV): 99.7% fl. R epimer, 0.2% fl. S epimer; q-NMR: R epimer 99.0%; m.p.: 210° C.; water content (KF): 0.5%; ignition residue: <0.1%.

Mixture B: 200 ml of ethanol are added to 160 g of industrial-grade ciclesonide (from Example 5, mixture B) and the mixture is heated to 70° C. with stirring. After the addition of 2 g activated charcoal it is filtered hot and the filter residue is washed with 115 ml of ethanol. The combined filtrate is left to cool to ambient temperature. The resulting crystal suspension is stirred for several hours at ambient temperature, cooled to 0° C. and kept for 2 h at 0° C. The crystals separated by suction filtration are washed with 160 ml of cold ethanol and then dried at 60° C. in the vacuum dryer. 129 g of pure ciclesonide are obtained. Chromatographic purity (HPLC-UV): 99.7% fl. R epimer, 0.2% fl. S epimer; m.p.: 210-211° C.

Example 7

Isobutoxide Salt Screening 1 g aliquots of industrial grade compound 2 (with an epimer ratio R/S of 97.2:2.8) are dissolved in 5 ml of solvent at ambient temperature, combined with 1.4 equivalents of isobutoxide salt and stirred at 50° C. Conversion monitoring using HPLC-UV is carried out after 1 h, 2 h and 5 h. For results: see the Table.

What is claimed is:

1. A process for preparing ciclesonide of formula 1,

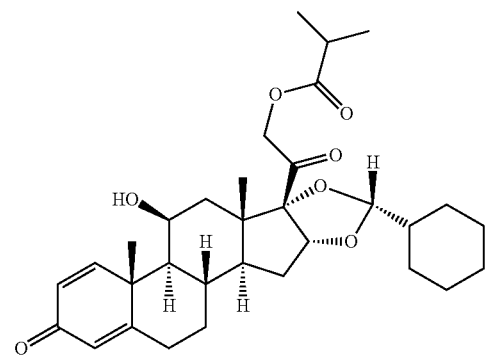

characterized in that a compound of formula 2

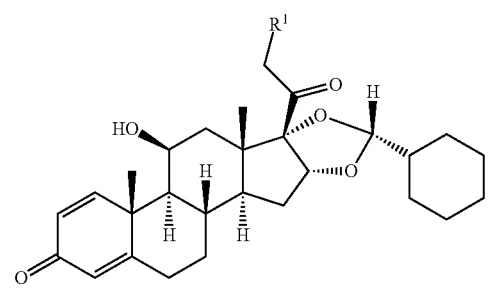

wherein $R^1$ is Br, is reacted with a salt of formula

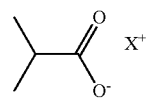

wherein $X^+$ denotes alkali metal ions or $N(R^2)_4^+$, wherein $R^2$ denotes $C_{1-6}$-alkyl and further characterized in that the compound of formula 2 is prepared by a regioselective bromination of a compound of formula 3

| isobutoxide salt | solvent | after 1 h: educt/R/S* | after 2 h: educt/R/S* | after 5 h: educt/R/S* |
|---|---|---|---|---|
| sodium isobutoxide | NMP | 0.7/97.7/1.6 | <0.1/97.7/2.2 | <0.1/97.1/2.8 |
| potassium isobutoxide | NMP | <0.1/97.1/2.8 | <0.1/97.0/2.9 | <0.1/97.2/2.7 |
| lithium isobutoxide | NMP | 19.9/79.5/0.6 | 4.0/94.8/1.2 | 0.1/98.0/1.9 |
| caesium isobutoxide | NMP | <0.1/97.0/2.9 | <0.1/97.0/2.9 | <0.1/97.0/2.9 |
| tetra-n-butylammonium isobutoxide | NMP | <0.1/96.9/3.0 | <0.1/97.5/2.4 | <0.1/97.6/2.3 |
| tetramethylammonium isobutoxide | NMP | <0.1/96.9/3.0 | <0.1/97.0/2.9 | <0.1/97.0/2.9 |
| sodium isobutoxide | DMSO | <0.1/97.3/2.6 | <0.1/97.1/2.8 | <0.1/97.1/2.8 |

*% Fl. compound 2/% Fl. ciclesonide/% Fl. 16α,17-[(S)-cyclohexylmethylenedioxy]-11β-hydroxy-21-(2-methyl-1-oxopropoxy)-pregna-1,4-dien-3,20-one

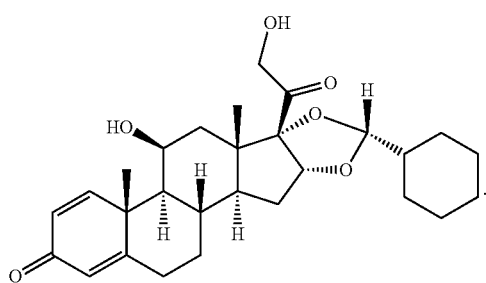

2. The process according to claim 1, wherein the regioselective bromination of the compound of formula 3 is carried out with a catalytic variant of the Appel reaction, with $PBr_3$, with $BrPPh_3Br$ or with mixtures of triphenylphosphine and an agent selected from among N-bromosuccinimide, tetrabromomethane, hexabromoacetone and $Br_2$.

3. The process according to claim 1, wherein the regioselective bromination of the compound of formula 3 is carried out in a solvent selected from among halohydrocarbons, nitriles and mixtures of halohydrocarbons and nitriles.

4. The process according to claim 1, characterized in that after the reaction has taken place the compound of formula 2 wherein $R^1$ denotes Br is purified by one or more crystallizations from a polar, water-miscible organic solvent or mixtures thereof, with or without the addition of water.

5. The process according to claim 4, characterized in that after the crystallization has taken place the compound of formula 2 wherein $R^1$ denotes Br is suspended in a polar, water-miscible organic solvent or mixtures thereof, with or without the addition of water, for further purification.

6. The process according to claim 1, wherein the compound of formula 3 is prepared by a reaction of the compound of formula 4

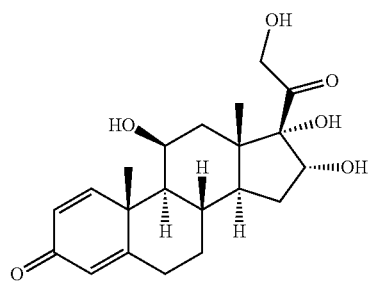

with cyclohexane aldehyde in the presence of an acid.

7. The process according to claim 6, wherein the product of formula 3 is not isolated.

8. The process of claim 6 wherein the acid used in the reaction of the compound of formula 4 with cyclohexane aldehyde is methanesulphonic acid.

* * * * *